United States Patent
Teng et al.

(10) Patent No.: US 7,172,906 B2
(45) Date of Patent: Feb. 6, 2007

(54) REDUCTION OF NON-SPECIFIC BINDING IN ASSAYS

(75) Inventors: Zhu Teng, Boothwyn, PA (US); Jeffrey L. Moore, Newark, DE (US); Alan R. Craig, Wilmington, DE (US); Gary Hickey, Hockessin, DE (US); Carsten Schelp, Hockessin, DE (US); Tie Quan Wei, Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 60 days.

(21) Appl. No.: 10/989,677

(22) Filed: Nov. 16, 2004

(65) Prior Publication Data

US 2006/0105472 A1    May 18, 2006

(51) Int. Cl.
| | | |
|---|---|---|
| G01N 33/548 | (2006.01) | |
| G01N 33/544 | (2006.01) | |
| G01N 33/547 | (2006.01) | |
| G01N 33/53 | (2006.01) | |
| G01N 1/17 | (2006.01) | |

(52) U.S. Cl. ............... 436/529; 436/528; 436/532; 435/7.1; 435/7.92; 530/402

(58) Field of Classification Search ............ 436/528, 436/529, 532; 530/402; 435/7.1, 7.92
See application file for complete search history.

(56) References Cited

U.S. PATENT DOCUMENTS

| | | | |
|---|---|---|---|
| 4,166,102 A | 8/1979 | Johnson | |
| 4,264,766 A | 4/1981 | Fischer | |
| 4,450,231 A | 5/1984 | Ozkan | |
| 4,452,773 A | 6/1984 | Molday | |
| 4,650,751 A | 3/1987 | Siegal et al. | |
| 4,914,040 A | 4/1990 | Lenz et al. | |
| 5,177,059 A | 1/1993 | Handley et al. | |
| 5,705,338 A | 1/1998 | Piran et al. | |
| 5,728,588 A | 3/1998 | Caldwell et al. | |
| 5,776,706 A | 7/1998 | Siiman et al. | |
| 6,011,008 A | 1/2000 | Domb et al. | |
| 6,399,317 B1 | 6/2002 | Weimer | |
| 6,489,309 B1 | 12/2002 | Singh et al. | |
| 6,500,930 B2 | 12/2002 | Adamson | |
| 6,646,120 B1 | 11/2003 | Chaubet et al. | |
| 6,949,524 B2 * | 9/2005 | Singh et al. ............ 514/54 |
| 2002/0034827 A1 | 3/2002 | Singh et al. | |
| 2003/0190760 A1 | 10/2003 | Watkins et al. | |
| 2004/0043508 A1 | 3/2004 | Frutes et al. | |

FOREIGN PATENT DOCUMENTS

WO    WO 99/07744    *    2/1999

* cited by examiner

*Primary Examiner*—Long V. Le
*Assistant Examiner*—Shafiqul Haq
(74) *Attorney, Agent, or Firm*—Theodore J. Leitereg

(57) ABSTRACT

Methods and compositions are disclosed for reducing non-specific binding in a binding assay for the determination of an analyte in a sample where one of the reagents for conducting the binding assay comprises a solid support comprising a polysaccharide. The method comprises including in an assay medium for conducting the binding assay a soluble compound comprising a protein linked to a polysaccharide. Also disclosed are methods and compositions for determining the presence and/or amount of an analyte in a sample suspected of containing the analyte. The methods include as reagents a solid support comprising a polysaccharide and a soluble compound comprising a protein linked to a polysaccharide.

21 Claims, No Drawings

REDUCTION OF NON-SPECIFIC BINDING IN ASSAYS

BACKGROUND OF THE INVENTION

In the fields of medicine and clinical chemistry, many studies and determinations of physiologically reactive species such as cells, proteins, enzymes, cofactors, nucleic acids, substrates, antigens, antibodies, and so forth are carried out using conjugates involving specific binding pair members or labels or the like. Various assay techniques that involve the binding of specific binding pair members are known. These assay techniques generally also involve a label used in the detection part of the assay.

Polysaccharides, particularly dextran, have been conjugated to specific binding pair members, for example, to increase the stability of the specific binding pair member. In some approaches, a polysaccharide is bound to a surface of a support and a specific binding pair member is linked to the polysaccharide to provide a surface coated with polysaccharide and having a specific binding pair member attached thereto. Such supports are employed in assays for analytes. Conjugation of specific binding pair members to polysaccharides increases the bulkiness of these molecules, which can enhance their effectiveness in assays involving specific binding pair members by interfering with binding to complementary specific binding pair members. Additionally, these conjugates, when present on a surface, permit specific binding of a complementary specific binding pair member to the surface with reduced non-specific binding. The polysaccharide conjugates are employed in numerous types of assays, including homogeneous and heterogeneous assays and so forth, which are performed on biological samples such as blood, serum, and the like.

There are, however, certain samples such as, for example, serum samples, which produce a positive result independently of the presence or absence of an analyte in assays in which the aforementioned polysaccharide coated supports are employed. The likely explanation for this result is the non-specific binding of components from the sample to one or more of the assay reagents particularly the polysaccharide coated support with linked specific binding pair member. The non-specific binding can increase the reading of a positive test result, and in some instances, the non-specific binding can produce a positive reading when the analyte is absent, either case providing a misleading assay result.

One approach has been suggested for nonspecific IgG binding to a polymeric solid phase in an immunoassay of a serum sample. The approach involves the inclusion of a water-soluble polymer in the liquid phase where the water-soluble polymer is formed by polymerization of monomers that are the same as, or have approximately the same immunological binding affinity as, monomers of the polymer at the solid phase surface. Materials employed as the water soluble polymer included poly(styrene-alt-maleic acid) and poly(acrylic acid), which demonstrated superiority over poly(methacrylic acid) and dextran and a number of other materials.

There remains a need for agents for blocking non-specific binding in assays involving polysaccharide conjugates linked to a support

SUMMARY OF THE INVENTION

One embodiment of the present invention is a method for reducing non-specific binding in a binding assay for the determination of an analyte in a sample wherein one of the reagents for conducting the binding assay comprises a solid support comprising a polysaccharide. The method comprises including in an assay medium for conducting the binding assay a soluble compound comprising a protein linked to a polysaccharide.

Another embodiment of the present invention is a method for determining the presence and/or amount of an analyte in a sample suspected of containing the analyte. A combination is provided that comprises the sample, a soluble compound comprising a protein linked to a polysaccharide, and reagents for detecting the analyte. At least one of the reagents for detecting the analyte is a support comprising a polysaccharide. The combination is incubated under conditions for binding of the analyte to one or more of the reagents. The presence and/or amount of binding of the analyte to one or more of the reagents is determined where the presence and/or amount of the binding is related to the presence and/or amount of the analyte in the sample.

Another embodiment of the present invention is a composition comprising a polysaccharide linked to a protein, wherein the linkage between the polysaccharide and the protein has substantially the same structure as the linkage used for linking the specific binding pair members to the surface of a solid phase reagent of an assay.

Another embodiment of the present invention is a protein-polysaccharide conjugate comprising repeating monosaccharide units and are of the formula:

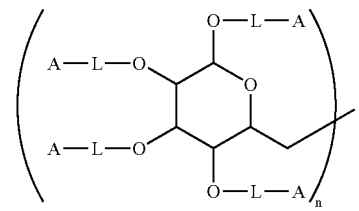

wherein one of the A's is a bond to the C1 glycosidic carbon (as indicated in the above formula) of another of the units, n is an integer of about 3 to about 50,000, the other A's are independently selected from the group consisting of protein molecules, hydrogen, groups imparting water solubility, or crystallinity reducing substituents, and L is a bond or a linking group, and the ratio of protein molecules to monosaccharide molecules is in the range of about 1:2 to about 1:100.

In some embodiments, when L is a linking group and A is a protein, L-A has the formula:

wherein m is an integer of 0 to about 5, R and R' are independently selected from the group consisting of hydrogen, lower alkyl, and aryl, or R and R' may be taken together to form a double bond.

DESCRIPTION OF THE SPECIFIC EMBODIMENTS

As mentioned above, in one aspect a method is provided for reducing non-specific binding in a binding assay for the determination of an analyte in a sample wherein one of the reagents for conducting the binding assay comprises a solid support comprising a polysaccharide. The method comprises including in an assay medium for conducting the binding assay a soluble compound comprising a protein linked to a polysaccharide.

Non-specific binding, in general, means non-covalent binding between molecules that is relatively independent of specific surface structures. Non-specific binding is distinguished from specific binding, which involves the specific recognition of one of two different molecules for the other compared to substantially less recognition of other molecules. Non-specific binding may result from several factors including hydrophobic interactions between molecules, electrostatic or ion exchange interactions between molecules, species-specific interactions between molecules (e.g., human anti-mouse antibody, mouse anti-sheep antibody, and the like), and so forth. The nature of the molecule or molecules that result in non-specific binding in assays is dependent on the nature of the sample, the assay milieu, the solid phase reagent surface, and so forth. For the most part the non-specific binding molecules are protein materials such as, for example, non-specific immunoglobulins, immunoglobulins having specificity to molecules other than the analyte of the assay, complement cascade proteins, clotting cascade proteins, and the like. The sample may be biological tissue, which includes excised tissue from an organ or other body part of a host and body fluids, for example, whole blood, plasma, serum, urine, saliva, semen, stool, sputum, cerebral spinal fluid, tears, mucus, and the like. In many instances, the sample is plasma or serum.

The binding assay generally involves specific binding between molecules. The molecules may be referred to as members of a specific binding pair ("sbp"), which means one of two different molecules, having an area on the surface or in a cavity, which specifically binds to and is thereby defined as complementary with a particular spatial and polar organization of the other molecule. The members of the specific binding pair may also be referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the definition of sbp member. Binding assays are discussed in more detail below.

The reagents for conducting the binding assay usually include one or more sbp members, which may or may not be bound to other molecules depending on the nature of a particular assay in which the reagents are employed. One or more specific binding pairs may be utilized depending on the nature of the assay. The sbp member may or may not be bound to a support, a member of a signal producing system such as a label, an sbp member from a different specific binding pair, and so forth. Accordingly, the reagents for conducting an assay may include additional sbp members, ancillary reagents such as an ancillary enzyme substrate, signal producing system members, buffers, blocking agents for other forms of non-specific binding, and so forth. The reagents utilized for conducting a binding assay depend on the nature of the assay to be conducted and are discussed in detail below with respect to various assay embodiments. One or more particulate reagents may be employed in an assay depending on the nature of the assay.

One of the reagents for conducting a binding assay is a support comprising a polysaccharide, which is a carbohydrate containing three or more monosaccharide units. The polysaccharide can be straight-chained or branched. The molecular weight (in Daltons) of the polysaccharide is about 10,000 to about 5 million or more, and in some instances 10,000 to about 1 million or more, and in some instances about 10,000 to about 500,000, and in some instances about 30,000 to about 350,000.

Examples of polysaccharides by way of illustration and not limitation are dextran, dextran derivatives, cyclodextrin, cellulose derivatives, agarose, gums, starch, glycogen, polyribose, amylose, and the like. A monosaccharide is a carbohydrate that cannot be hydrolyzed into simpler compounds such as an aldehyde alcohol or a ketone alcohol, e.g., a hexose or a pentose. Dextran is a polysaccharide consisting of linear 1–6 linked (98%) glucose units and may be referred to as a polymerized glucose. Dextran derivatives are dextran modified by cross-linking, degradation, functionalization, or the like, such as, for example, modification of one or more hydroxyl groups by linking to another moiety or by modification to a different functional group such as, for example, carboxyl, sulfate, sulfite, sulfone, amide, sulfonamide, halomethylcarbonyl, epoxide, amino, aldehyde, active ester, maleimide, and the like. Where the polysaccharide is not water soluble, the modification may include one or more groups or functionalities imparting water solubility as discussed below.

The nature of the polysaccharide-support reagent is primarily dependent on the nature of the binding assay. In many instances the polysaccharide is non-diffusively bound to the surface of a support. Polysaccharide may be non-diffusively bound to the surface of a support either covalently (by direct bond to the polysaccharide or by a linking group) or non-covalently (by adsorption, precipitation (e.g. agarose), and the like) as long as the polysaccharide remains substantially bound to the surface under the conditions of an assay or other conditions to which such supports are subjected. Approaches for coating a surface of a support with a polysaccharide are known in the art. For example, approaches are discussed in Immunological Diagnostic Reagents, U.S. Pat. No. 4,264,766, Ernst A. Fischer, Apr. 28, 1981, the relevant portions of which are incorporated herein by reference.

The support is generally a solid phase, which is usually a porous or non-porous water insoluble material that can have any one of a number of shapes, such as strip, rod, plate, well, particle or bead, and so forth. A wide variety of suitable supports are disclosed in Ullman, et al., U.S. Pat. No. 5,185,243, columns 10–11, which is incorporated herein by reference.

The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, glass fiber paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass such as, e.g., glass available as Bioglass, ceramics, metals, and the like. Natural or synthetic assemblies such as liposomes, phospholipid vesicles, and cells can also be employed. The support may include molded parts such as, for example, wells of a microtiter well plate, paddles, spheres, and so forth.

Particles may be uniform or non-uniform in shape and may be microscopic or macroscopic in size. The particles may be of at least about 20 nm and not more than about 20 microns, and in some instances, at least about 40 nm and less than about 10 microns, and in some instances from about 0.10 to 2.0 microns diameter. The particle may have any density, but preferably of a density approximating water, generally from about 0.7 to about 1.5 g/ml. The particles may or may not have a charge, and when they are charged, they are preferably negative. The particles may be solid (e.g., comprised of organic and inorganic polymers or latex), oil droplets (e.g., hydrocarbon, fluorocarbon, silicon fluid), or vesicles (e.g., synthetic such as phospholipid or natural such as cells and organelles).

The solid particles are normally polymers, either addition or condensation polymers, which are readily dispersible in the assay medium. The solid particles are also adsorptive or functionalizable so as to bind or attach at their surface, either directly or indirectly, a polysaccharide, a polysaccharide—sbp member conjugate, or the like, and in some instances to incorporate within their volume a reactive reagent. The particles may be non-magnetic or magnetic.

The solid particles can be comprised of polystyrene, polyacrylamide, homopolymers and copolymers of derivatives of acrylate and methacrylate, particularly esters and amides, silicones and the like. Oil droplets are water-immiscible fluid particles comprised of a lipophilic compound coated and stabilized with an emulsifier that is an amphiphilic molecule such as, for example, phospholipids, sphingomyelin, albumin and the like that exist as a suspension in an aqueous solution, i.e. an emulsion. Liposomes are microvesicles comprised of one or more lipid bilayers having approximately spherical shape and one of the preferred materials for use in the present invention.

Latex particles are a particulate water suspendable, water insoluble polymeric material usually having particle dimensions of 20 nm to about 2000 nm, in some instances about 100 to about 1000 nm in diameter. The latex may be a substituted polyethylene such as polystyrene-butadiene, polyacrylamide polystyrene, polystyrene with amino groups, substituted poly-acrylic acid, substituted polymethacrylic acid, acrylonitrile-butadiene, styrene copolymers, polyvinyl acetate-acrylate, vinyl-chloride acrylate copolymers, and the like. Non-crosslinked polymers of styrene and carboxylated styrene or styrene functionalized with other active groups such as amino, hydroxyl, halo and the like are preferred. In some instances, copolymers of substituted styrenes with dienes such as butadiene will be used.

As mentioned above, in order to reduce non-specific binding in a binding assay for the determination of an analyte in a sample wherein one of the reagents for conducting the binding assay comprises a solid support comprising a polysaccharide, a soluble compound comprising a protein linked to a polysaccharide is present in the assay medium. The polysaccharide of the soluble compound may be selected from the polysaccharides mentioned above and may be the same as, or different from, the polysaccharide on the support. When the polysaccharides are different, they may differ by being derived from different derivatives of the same polysaccharide or they may differ by comprising different monosaccharide units in the polymeric chain. When different, the polysaccharide of the soluble compound may differ by being chemically structurally similar but of differing molecular weights. The molecular weight (in Daltons) of the polysaccharide of the soluble compound should be about 10,000 to about 1,000,000, or about 40,000 to about 500,000 or the like. In other situations where the polysaccharides are different, the polysaccharide of the soluble conjugate should have the characteristic of being capable of binding to the same binding site of the interfering binder found in the discrepant samples that binds to the polysaccharide on the support.

The polysaccharide-protein conjugate is soluble in the assay medium in which it is employed. The solubility of the conjugate is dependent on the nature of the assay medium, the temperature of the assay medium, factors that determine the presence of crosslinking of the conjugate such as the starting molecular weight of the protein and the polysaccharide, as well as the stoichiometry of the polysaccharide and the protein used in the synthesis of the conjugate, and so forth. In many instances, the assay medium is an aqueous medium, usually, an aqueous buffered medium. The aqueous medium may be solely water or may include from about 0.01 to about 80 volume percent, and in some instances, about 0.1 to about 40 volume percent, of a cosolvent. The cosolvent may be an oxygenated hydrocarbon such as, for example, an alcohol, an ether, an amide, a ketone, and the like. Lower alkyl alcohols such as, for example, methanol, ethanol, propanol and so forth may be employed. The pH for the medium is generally a moderate pH and is the range of about 4 to about 11, or in the range of about 5 to about 10, or in the range of about 6.5 to about 9.5. The pH will usually be a compromise between optimum binding of the binding members of any specific binding pairs, the pH optimum for other reagents of the assay such as members of the signal producing system, and so forth.

Various buffers may be used to achieve the desired pH and maintain the pH during the assay. Illustrative buffers include borate, phosphate, carbonate, tris, barbital and the like. Various ancillary materials may be employed in the assay medium. For example, in addition to buffers the medium may comprise stabilizers for the medium and for the reagents employed. In some instances, in addition to these additives, proteins may be included, such as albumins; polyanions such as dextran sulfate; surfactants, particularly non-ionic surfactants; binding enhancers, e.g., polyalkylene glycols; or the like. Some additives, such as some other water soluble polymers and some salts at high concentration may render the conjugates insoluble due to incompatibility, so their use would be precluded with the polysaccharide-protein conjugates.

The practical limit of concentration of the polysaccharide-protein conjugate is determined by the viscosity of the solution of the conjugate in buffer, which will, in turn, be affected by the molecular weight of the conjugate. The practical viscosity limit for conjugates of molecular weight 10 million is in the range of about 1 to about 5%.

In many embodiments where the assay medium is aqueous, the polysaccharide-protein conjugate is water soluble. The term "water-soluble" is used herein to refer to freely soluble in water at essentially all proportions as well as those of only limited solubility, i.e., limited to the extent mentioned above. Conjugates of limited water solubility can be employed, where appropriate, at concentrations below their solubility limits.

If the components of the conjugate are not already water soluble so that the resulting conjugate is water soluble, one or both of the components may be functionalized to impart water solubility to the conjugate by incorporating one or more groups or functionalities that impart hydrophilicity. One of skill in the art may readily determine the appropriate substitution, taking into consideration the desired effect and/or materials that are readily available. Such a group or functionality is in many instances a hydrophilic functionality, which increases wettability of solids with water and the solubility in water of compounds to which it is bound. Such functional group or functionality can be a substituent having 1 to 50 or more atoms and can include a group having a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of the polysaccharide to a protein or vice versa.

It should be noted that the polysaccharide of the soluble compound and the polysaccharide on the support are sometimes referred to herein and in the accompanying claims as first polysaccharide and second polysaccharide. This designation is made to distinguish between polysaccharide on the support and polysaccharide of the soluble compound, which may be different. The designation is purely arbitrary and is not meant to convey any order of preference, addition, or the like to the polysaccharide(s) employed.

The protein component of the soluble compound may be any protein that, when part of the soluble compound and used as discussed herein, will result in a reduction of non-specific binding in an assay. The nature of the protein employed is dependent on the nature of the sample to be analyzed, the molecular weight of the protein, its chemical reactivity, its solubility properties, and so forth. In most instances, the protein of the soluble compound is a one that will not interfere with an assay for an analyte. Therefore, the protein should not be a specific binding pair member for any reagent or analyte of an assay or any component of a sample to be analyzed. The protein may be of animal (including insect, fish, fowl and so forth) or vegetable origin. Suitable animal proteins include proteins from blood, serum, plasma, digested collagen, and the like. Suitable vegetable proteins include pumpkin seed globulin, and the like. Blood proteins include, by way of illustration and not limitation, gamma globulins, such as goat, bovine, sheep, and mouse gamma globulin; albumins such as bovine serum albumin, human serum albumin, ovalbumin, and so forth. Examples of other proteins include casein; gelatins such as enzymatic gelatin hydrolysate, fish gelatin, and fish skin gelatin; and the like.

In the conjugate, the number of protein molecules per polysaccharide is dependent upon concentrations of activated species during conjugation, degree of activation of species, size and shape of polysaccharide derivative, size and shape of the protein, and so forth. One skilled in the art may readily determine the appropriate substitution, taking into consideration the desired effect and/or materials that are readily available. The ratio of polysaccharide molecules to protein molecules in the conjugate is generally about 5 to about 1, about 4 to about 1, about 3 to about 1, about 2 to about 1, about 1 to about 1, about 1 to about 2, about 1 to about 3, about 1 to about 4, about 1 to about 5, and so forth. In general, the ratio will depend on the nature of the polysaccharide such as, e.g., the chemical composition, molecular weight, etc., and on the nature of the protein such as, e.g., chemical composition, molecular weight, etc., and in some instances may be determined empirically.

A wide variety of techniques may be employed to link the polysaccharide and the protein to form the soluble compound. In one approach, a polysaccharide is treated by known oxidative methods (e.g., activation with periodate, perbromate, and the like) to yield an oxidative form wherein at least a portion of the saccharide monomeric units are oxidized to present aldehyde groups. The oxidized polysaccharide so formed is then reacted with a protein, which through primary amine groups reacts with the aldehyde groups of the oxidized polysaccharide and covalently binds to the polysaccharide through Schiff base linkages. This type of reaction is also referred to as reductive amination.

Another example involves an amino derivatized polysaccharide or a carboxylmethyl polysaccharide, which reacts with a protein to form an amide product. For example, aminodextran or carboxymethyldextran have usually been utilized for forming conjugates to specific binding pair members. Coupling the dextran to a protein, for example, can then be carried out through formation of an amide.

A variety of antibody-aminodextran conjugates are described in U.S. Pat. No. 5,527,713 and U.S. Pat. No. 5,658,741. Such techniques may be employed to link proteins to polysaccharides in general. Recently, polymeric carriers containing the divinyl sulfone moiety for covalent attachment of protein and other molecular species were described in European Patent No. 0 594 772 B1.

Aminodextran can be prepared by methods described in U.S. Pat. No. 5,466,609 and U.S. Pat. No. 5,527,713, by periodate oxidation of dextran followed by reaction with 1,3-propanediamine. Of course, the particular method of making the aminodextrans is not limited to such techniques and it is envisioned that any technique for making such aminodextrans are well within the knowledge of those of skill in the art. For example, one of skill in the art may readily substitute a diaminoalkane having two to six carbons for 1,3-propanediamine described in the examples. Preferably, the aminodextran is 5x-Amdex or 1x-Amdex, and most preferably 5x-Amdex.

The linking group may be a chain of from 1 to about 30 or more atoms, from about 1 to about 20 atoms, about 1 to about 10 atoms, each independently selected from the group normally consisting of carbon, oxygen, sulfur, nitrogen, and phosphorous, usually carbon and oxygen. The number of heteroatoms in the linking group normally ranges from about 0 to about 8, from about 1 to about 6, about 2 to about 4. The number of atoms in the chain is determined by counting the number of atoms other than hydrogen or other monovalent atoms along the shortest route between the substructures being connected. The atoms of the linking group may be substituted with atoms other than hydrogen such as carbon, oxygen and so forth in the form, e.g., of alkyl, aryl, aralkyl, hydroxyl, alkoxy, aryloxy, aralkoxy, and the like. As a general rule, the length of a particular linking group can be selected arbitrarily to provide for convenience of synthesis with the proviso that there be minimal interference caused by the linking group with the ability of the linked molecules to perform their function related to the assay in question.

The linking group may be aliphatic or aromatic. When heteroatoms are present, oxygen will normally be present as oxy or oxo, bonded to carbon, sulfur, nitrogen or phosphorous; sulfur will be present as thioether or thiono; nitrogen will normally be present as nitro, nitroso or amino, normally bonded to carbon, oxygen, sulfur or phosphorous; phosphorous will be bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth.

Examples, by way of illustration and not limitation, of various linking groups that find use in the present invention are found in U.S. Pat. No. 3,817,837, particularly at column 30, line 69, to column 36, line 10, which disclosure is incorporated herein by reference in its entirety. Various linking groups and linking functionalities are disclosed in Cautrecasas, *J. Biol. Chem.* (1970) 245:3059. Examples of commercially available cross-linking reagents are disclosed in the Pierce Catalog and Handbook, Life Science and Analytical Research Products, Pierce Chemical Company, Rockford, Ill., 1994/1995.

The compounds according to the invention can be purified with conventional methods, for example, chromatography, filtration including microfiltration, ultrafiltration, diafiltration, etc., precipitation, dialysis, and the like.

The soluble protein-polysaccharide conjugate usually carries a neutral charge or a negative charge. If the charge of the soluble protein-polysaccharide conjugate is not neutral, it is desirable that the soluble compound have the same charge as the support reagent comprising a polysaccharide. The support reagent comprising a polysaccharide usually has a negative charge and, thus, the soluble protein-polysaccharide conjugate should have a negative or neutral charge.

One or more of the reagents for conducting an assay, other than the soluble compound or a support comprising a polysaccharide, may include an additional support reagent, which may or may not comprise a polysaccharide. If the additional support reagent comprises a polysaccharide, the polysaccharide may be the same as or different from the polysaccharide of the other support reagent or of the soluble compound. For example, two or more sets of particle reagents may be employed in an assay depending on the assay format. One or more of the particle reagents may comprise a polysaccharide. One particle reagent may be coated with a polysaccharide, which is linked to one sbp member of a specific binding pair, and another particle reagent may be coated with a polysaccharide, which is linked to another sbp member from a different specific binding pair. It should be obvious to one skilled in the art that numerous assay formats are possible where a soluble protein-polysaccharide conjugate may be employed to avoid non-specific binding in an assay.

It is usually desirable that the affinity binding behavior of the soluble compound is greater than the affinity binding behavior of the polysaccharide on the support. The phrase "affinity binding behavior" relates to affinity strength and specificity in the types of interactions that typically constitute immunological or affinity binding such as, for example, antigen-antibody-type binding. In some embodiments the affinity binding behavior of the soluble compound is greater that the affinity binding behavior of the polysaccharide on the support by at least about 2 times, at least about 3 times, at least about 4 times, at least about 5 times, at least about 10 times, at least about 15 times, at least about 20 times, at least about 30 times, at least about 40 times, at least about 50 times, at least about 100 times, at least about 150 times, at least about 200 times, at least about 250 times, at least about 300 times, or more.

The amount of soluble protein-polysaccharide compound employed is usually an amount sufficient to reduce significantly or eliminate interference from non-specific binding in specific binding assays. A significant reduction of interference from non-specific binding is achieved when an assay response is greater than that achieved in the absence of the soluble protein-polysaccharide conjugate and whether or not in the presence of components of the conjugate separate from the conjugate such as protein alone or polysaccharide alone or a combination of separate protein and separate polysaccharide and whether or not other materials for reducing interference are present. The amount of soluble compound used in any particular assay is usually determined empirically. Usually, the soluble compound is employed in an excess amount. The amount of soluble compound may be about 0.1 to about 5 mg/mL, in some instances about 0.5 to about 2 mg/mL, in the assay medium. However, the above amounts are by way of illustration and not limitation. Amounts outside the above ranges may be employed in certain circumstances as long as the amount is sufficient to reduce significantly or eliminate interference from non-specific binding in specific binding assays.

Specific Embodiments of Protein-Polysaccharide Conjugates

Specific embodiments of exemplary soluble compounds are discussed next by way of illustration and not limitation.

In some embodiments the protein-polysaccharide conjugates comprise repeating monosaccharide units and are of the formula:

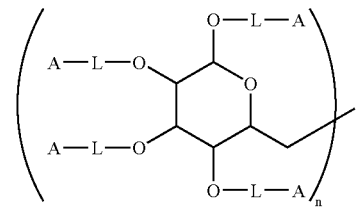

wherein one of the A's is a bond to the C1 glycosidic carbon (as indicated in the above formula) of another of the units, n is an integer of about 3 to about 50,000, or about 25 to about 10,000, or about 50 to about 1,000, L is a bond or a linking group as defined above and the other A's are independently selected from the group consisting of protein molecules, hydrogen, groups imparting water solubility, or crystallinity reducing substituents.

The term "crystallinity reducing substituents" refers to groups or functionalities that reduce or eliminate crystallinity from the parent backbone of the polysaccharide thereby increasing the solubility of the polysaccharide or subsequent conjugate. Crystallinity reducing substituents include, for example, carboxymethyl substituents (e.g., on cellulose and the like), methyl, hydroxyethyl, and the like.

The number of A's that are protein molecules is dependent on factors such as the size of the protein molecule and so forth. In some embodiments the ratio of protein molecules to monosaccharide molecules is in the range of about 1:2 to about 1:100, or about 1:3 to about 1:95, or about 1:4 to about 1:90, or about 1:5 to about 1:85, or about 1:6 to about 1:80, or about 1:7 to about 1:75, or about 1:8 to about 1:70, or about 1:9 to about 1:65, or about 1:10 to about 1:60, or about 1:15 to about 1:55, or about 1:20 to about 1:50, or about 1:25 to about 1:45, or about 1:30 to about 1:40. In some embodiments one of the A's is a protein molecule for at least every two monosaccharide molecules, for at least about every three monosaccharide molecules, for at least about every four monosaccharide molecules, for at least about every five monosaccharide molecules, for at least about every six monosaccharide molecules, for at least about every seven monosaccharide molecules, for at least about every eight monosaccharide molecules, for at least about every nine monosaccharide molecules, for at least about every ten monosaccharide molecules, for at least about every fifteen monosaccharide molecules, for at least about every twenty monosaccharide molecules, for at least about every twenty five monosaccharide molecules, for at least about every thirty monosaccharide molecules, for at least about every thirty five monosaccharide molecules, for at least about every forty monosaccharide molecules, for at least about every forty five monosaccharide molecules, for at least about every fifty monosaccharide molecules, and so forth.

In some embodiments, when A is a protein, L is a linking group of the formula, which includes the protein moiety:

—$CH_2(CH_2)_m CHR'$—NR-protein wherein R and R' are independently selected from the group consisting of hydrogen, lower alkyl, aryl, and the like or R and R' may be taken together to form a double bond between CH and N (i.e., —$CH_2(CH_2)_m CH=N$—) and wherein m is an integer of 0 to about 5, about 1 to about 5, about 1 to about 4, about 1 to about 3, about 1 to about 2, and wherein the nitrogen is from an amino acid of the protein.

In some embodiments, when A is a protein, L is a linking group of the formula:

—$CH_2(CH_2)_m CH_2$—NR—$CH_2(CH_2)_p CH_2$— wherein m and p are independently integers of 0 to about 5, about 1 to about 5, about 1 to about 4, about 1 to about 3, about 1 to about 2, and R is selected from the group consisting of hydrogen, lower alkyl, aryl, and the like. In some embodiments the linking group L is formed by the reaction of a linking group on the polysaccharide comprising a terminal aldehyde group and a nitrogen group of the protein molecule such as, for example, a nitrogen group of an amino acid residue of the protein molecule. Accordingly, the —NR—$CH_2(CH_2)_p CH_2$— portion of the above linking group may come from an amino acid residue of the protein such as, for example, a lysine (where the linking group comprises —NR—$CH_2(CH_2)_2 CH_2$—CH(COOH)NH— and the polysaccharide conjugate is polysaccharide-$CH_2$(CH_2)_3 CH_2$—NR—$CH_2(CH_2)_2 CH_2$—CH(COOH)NH-protein, and the like. In some embodiments the protein molecules are selected from the group consisting of albumins and gamma-globulins.

In some embodiments, when A is a protein, L is a linking group of the formula:

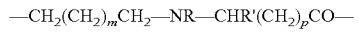
—$CH_2(CH_2)_m CH_2$—NR—CHR'$(CH_2)_p$CO— wherein m and p are independently integers of 0 to about 5, about 1 to about 5, about 1 to about 4, about 1 to about 3, about 1 to about 2 and R and R' are independently selected from the group consisting of hydrogen, lower alkyl, aryl, and the like. In some embodiments the linking group L is formed by the reaction of a linking group on the polysaccharide comprising a terminal aldehyde group and a nitrogen group of the protein molecule such as, for example, a nitrogen group of an amino acid residue of the protein molecule. Accordingly, the —NR—CHR'$(CH_2)_p$CO— portion of the above linking group may come from an amino acid residue of the protein such as, for example, the N-terminal amino acid of the protein, and the like. In some embodiments the protein molecules are selected from the group consisting of albumins and gamma-globulins.

In some embodiments the protein-polysaccharide conjugates are protein-dextran conjugates of the formula:

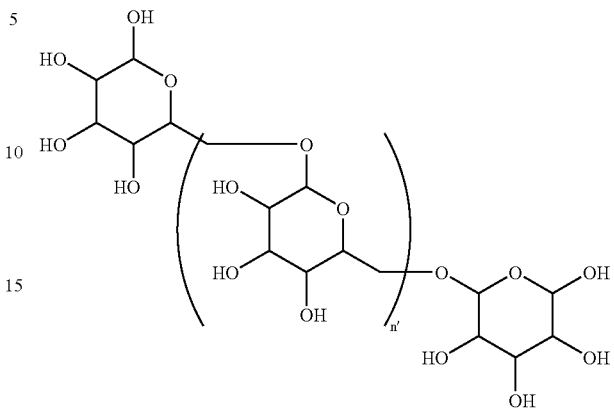

wherein one or more of the n' monosaccharide units have the formula:

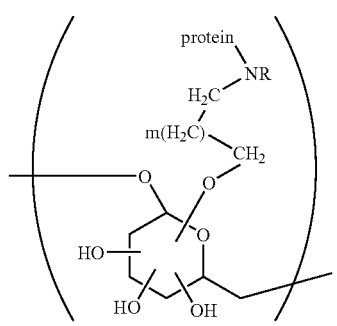

protein-substituted monosaccharide and wherein n' is an integer of about 3,000 to about 60,000, m is as defined above, R is as defined above, protein is, for example, a gamma globulin or an albumin, and wherein the protein —NR-protein may be —NR—$CH_2(CH_2)_p CH_2$-protein wherein p is a defined above and wherein the —NR—$CH_2(CH_2)_p CH_2$— portion of the above linking group may come from an amino acid residue of the protein such as, for example, a lysine, and the like, or wherein the —NR-protein may be —NR—CHR'$(CH_2)_p$CO-protein wherein the —NR—CHR'$(CH_2)_p$CO— portion of the above linking group may come from an amino acid residue of the protein such as, for example, the N-terminal amino acid of the protein, and the like. The number of protein-substituted monosaccharide units is about 20 to about 500 for n' of about 3,000 to about 60,000 (corresponding to a molecular weight of about 10 million), and the like, by way of example and not limitation.

In a specific embodiment of the above, m is 4, the —NR-protein is —NR—$CH_2(CH_2)_p CH_2$-protein wherein p is 2. In another specific embodiment of the above, —NR-protein is —NR—$CH_2(CH_2)_2 CH_2$—C(COOH)NH-protein.

The above protein-dextran conjugates may be synthesized from the corresponding dextran aldehyde, which reacts with an amino group on the protein such as, for example, an amino group of an N-terminal amino acid, e.g., a lysine, of the protein.

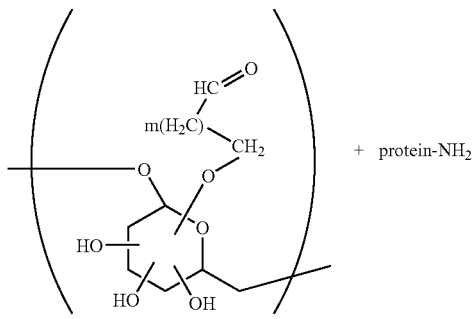 + protein-NH$_2$ dextran aldehyde portion of polysaccharide above

In an exemplary approach to the synthesis of dextran aldehyde by way of illustration and not limitation, dextran is combined in an aqueous medium under basic conditions with an appropriate dioxolane such as, for example, 2-(4-halobutyl)-1,3-dioxolane wherein halo is chloro, bromo or iodo. Basic conditions may be achieved by inclusion in the aqueous medium of a base such as, for example, sodium hydroxide, potassium hydroxide, or the like. The pH of the basic medium is greater than about 14. The reaction is carried out at elevated temperature of about 30° C. to about 100° C., or about 50° C. to about 90° C. for a time period of about 6 to about 48 hours, or about 12 to about 24 hours. Then, water is added and the mixture is cooled to room temperature. The pH is adjusted to about 5 to about 7, or about 6 to about 6.5, by addition of an acid such as, for example, a mineral acid, e.g., hydrochloric acid, and the like, or an organic acid, e.g., acetic acid, and the like. The resulting dextran aldehyde product may be subjected to various techniques for isolation and purification as discussed above.

Then, the dextran aldehyde is reacted with an amine of the protein. Generally, this reaction is carried out under mildly acidic conditions in the presence of a reducing agent such as cyanoborohydride or the like. The pH of the reaction medium containing the reactants should be low enough to permit an appreciable number of the amine groups to be protonated but not so low as to result in an insufficient amount of the free amine compounds. The pH is usually about 4 to about 7, or about 5 to about 6.5, or about 5.5 to about 6. The time period for the reaction is usually about 10 to 20 hours, preferably, about 14 to 18. The temperature of the reaction mixture is generally about 15 to 30° C., usually, about 20 to 25° C.

It is often desirable to quench any aldehyde functionalities that have not reacted with polypeptide. To this end, the conjugate produced above is treated with a suitable quenching reagent that will form a stable product with the remaining free aldehyde groups. Such a quenching agent can be, for example, hydroxylamine, semicarbazide, phenylhydrazine, hydrazine, sodium cyanide, carboxymethoxyamine, and the like. The resulting product is purified by conventional means such as, for example, ultrafiltration, precipitation, dialysis and so forth.

Other approaches for preparing the above conjugates include the following:

In one approach the polysaccharide is reacted with a suitable alkylating agent such as, for example, epichlorohydrin or divinylsulfone, to introduce epoxide or vinylsulfone amine reactive functionality.

In another approach an amine reactive functionality can be introduced through oxidation of the polysaccharide with periodate to generate aldehyde groups that are amine reactive.

In some instances it may be desirable to form the protein-polysaccharide conjugate in situ. This may be accomplished, in the case of dextran, for example, by adding dextran aldehyde to a medium containing the protein. Such a medium may be, for example, a serum sample that is to be analyzed. The protein for forming the conjugate may be present in the serum sample or it may be added prior to adding the dextran aldehyde. The soluble protein-polysaccharide conjugate formed in situ may be utilized where a somewhat lower blocking of sample interference may be tolerated in an assay. For the most part, soluble protein-polysaccharide conjugates formed as a separate entity and then added to the sample to be analyzed provide better protection against interfering substances and are better utilized for samples that are more challenging with respect to protection against such interfering substances.

As mentioned above, another embodiment of the invention is a composition comprising a polysaccharide linked to a protein, wherein the linkage between the polysaccharide and the protein has substantially the same structure as the linkage used for linking a specific binding pair member to a polysaccharide on the surface of a solid phase reagent of an assay. In accordance with this embodiment, the linkage has substantially the same structure if the chemical structure of the linkage is substantially the same. This linkage may be a bond or a linking group as discussed above. The linking group is substantially the same, for example, when there is a homologous relationship between the linking groups where the difference due to homology is no more than 3 carbon atoms, no more than 2 carbon atoms, no more than 1 carbon atom. If the linking group comprises one or more functional groups, the linking groups are substantially the same where the functional groups of one linking group are the same as the functional groups of the other linking group.

EXAMPLES OF ASSAYS EMPLOYING THE WATER SOLUBLE COMPOUNDS

As mentioned above, the soluble protein-polysaccharide compounds or conjugates discussed above can be utilized in binding assays for analytes. The assay methods usually involve a sample suspected of containing an analyte, which is combined in an assay medium with reagents for carrying out the assay. Such reagents include a support or solid phase that comprises a polysaccharide and may further comprise an sbp member. Other assay reagents can include a binding partner for the analyte if the sbp member on the solid support is not a binding partner for the analyte, analyte analogs, other solid supports to which one of the above reagents is bound, binding partners for sbp members, and so forth. One or more of the reagents may be part of a signal producing system where at least one of the reagents can be labeled. The reagents are chosen such that a signal is obtained from a label in relation to the presence or amount of analyte in the sample. The assay can be performed either without separation (homogeneous) or with separation (heterogeneous) of any of the assay compounds or products. Since solid supports are utilized, the assay is usually heterogeneous although homogeneous formats using such reagents are known.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In a typical competitive heterogeneous assay a support having an antibody for analyte bound thereto by means of a polysaccharide is contacted with a medium containing the sample and analyte analog conjugated to a detectable label such as an enzyme (the "conjugate"). Analyte in the sample competes with the conjugate for binding to the antibody. After separating the support and the medium, the label activity of the support or the medium is determined by conventional techniques and is related to the amount of analyte in the sample.

A typical non-competitive sandwich assay is an assay disclosed in David, et al., U.S. Pat. No. 4,486,530, column 8, line 6 to column 15, line 63, incorporated herein by reference. In this method, an immune sandwich complex is formed in an assay medium. The complex comprises the analyte, a first antibody (monoclonal or polyclonal) that binds to the analyte and a second antibody that binds to the analyte or a complex of the analyte and the first antibody. Subsequently, the immune sandwich complex is detected and is related to the amount of analyte in the sample. The immune sandwich complex is detected by virtue of the presence in the complex of a label wherein either or both the first antibody and the second antibody contain labels or substituents capable of combining with labels.

Sandwich assays find use for the most part in the detection of antigen and receptor analytes. In the assay the analyte is bound by two antibodies specific for the analyte and, thus, the assay is also referred to as the two-site immunometric assay. In one approach a first incubation of unlabeled antibody coupled to a support, otherwise known as the insolubilized antibody, is contacted with a medium containing a sample suspected of containing the analyte. After a wash and separation step, the support is contacted with a medium containing the second antibody, which generally contains a label, for a second incubation period. The support is again washed and separated from the medium and either the medium or the support is examined for the presence of label. The presence and amount of label is related to the presence or amount of the analyte. For a more detailed discussion of this approach see U.S. Pat. Nos. Re 29,169 and 4,474,878, the relevant disclosures of which are incorporated herein by reference.

In a variation of the above sandwich assay the sample in a suitable medium is contacted with labeled antibody for the analyte and incubated for a period of time. Then, the medium is contacted with a support to which is bound a second antibody for the analyte. After an incubation period, the support is separated from the medium and washed to remove unbound reagents. The support or the medium is examined for the presence of the label, which is related to the presence or amount of analyte. For a more detailed discussion of this approach see U.S. Pat. No. 4,098,876, the relevant disclosure of which is incorporated herein by reference.

In another variation of the above, the sample, the first antibody bound to a support and the labeled antibody are combined in a medium and incubated in a single incubation step. Separation, wash steps and examination for label are as described above. For a more detailed discussion of this approach see U.S. Pat. No. 4,244,940, the relevant disclosure of which is incorporated herein by reference.

The soluble protein-polysaccharide conjugates have application to all of the above assays. A particular example of an assay is described below by way of illustration and not limitation. Such assay is referred to as an induced luminescence immunoassay and is described in U.S. Pat. No. 5,340,716 (Ullman, et al.) entitled "Assay Method Utilizing Photoactivated Chemiluminescent Label" ("induced luminescence assay"), which disclosure is incorporated herein by reference. In one approach the assay uses a particle incorporating a photosensitizer and a label particle incorporating a chemiluminescent compound. The label particle is conjugated to an sbp member that is capable of binding to an analyte to form a complex, or to a second sbp member to form a complex, in relation to the presence of the analyte. If the analyte is present, the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed, which in turn is related to the amount of analyte present.

By way of further illustration, a chemiluminescent particle is employed, which comprises the chemiluminescent compound associated therewith such as by incorporation therein or attachment thereto. An sbp member that binds to the analyte is bound to a polysaccharide coating these particles. A second sbp member that binds to the analyte is part of a biotin conjugate. Streptavidin is conjugated to a second set of particles having a photosensitizer associated therewith. The binding of the streptavidin to this second set of particles (photosensitizer particles) may or may not involve a polysaccharide on the particles. The chemiluminescent particles are combined with a protein-polysaccharide conjugate as discussed above and this combination is mixed with a sample suspected of containing an analyte and the photosensitizer particles. The reaction medium is incubated to allow the particles to bind to the analyte by virtue of the binding of the sbp members to the analyte. Then, the medium is irradiated with light to excite the photosensitizer, which is capable in its excited state of activating oxygen to a singlet state. Because the chemiluminescent compound of one of the sets of particles is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence of the analyte.

Another particular example of an assay to which the present soluble conjugates have application is discussed in U.S. Pat. No. 5,616,719 (Davalian, et al.), which describes fluorescent oxygen channeling immunoassays.

In general, moderate to relatively high temperatures can be employed for carrying out an assay. The temperatures can be constant or varying and will depend on the type of assay conducted and the reagents utilized. Incubation temperatures will normally range from about 5 to about 100° C., from about 20 to about 95° C. Temperatures during measurements will generally range from 5 to about 100° C., from about 20 to about 95° C.

The concentration of analyte that may be assayed will generally vary from about $10^{-2}$ to about $10^{-15}$ M, from about $10^{-5}$ to about $10^{-12}$ M. Considerations, such as whether the assay is qualitative, semiquantitative or quantitative (relative to the amount of analyte present in the sample), the particular detection technique and the concentration of the analyte, and optimization of the binding between the specific binding materials normally determine the concentrations of the various reagents.

The concentrations of the various reagents in the assay medium are generally determined by the concentration range of interest of the analyte. However, the final concentration of each of the reagents is normally determined empirically to optimize the sensitivity of the assay over the range. That is, a variation in concentration of analyte that is of significance should provide an accurately measurable signal difference.

While the concentrations of the various reagents in the assay medium will generally be determined by the concentration range of interest of the analyte to be detected, the final concentration of each of the reagents will normally be determined empirically to optimize the sensitivity of the assay over the range. That is, a variation in concentration of the components to be detected that is of significance should provide an accurately measurable signal difference.

While the order of addition may be varied widely, there will be certain preferences depending on the nature of the assay. The simplest order of addition is to add all the materials simultaneously. When not simultaneous, in some embodiments the sample and the soluble compound are mixed together prior to forming a combination with other assay reagents. In some embodiments the soluble compound and the solid support are mixed together prior to forming a combination with other assay reagents.

Other assay reagents can be combined wholly or partially sequentially. One or more incubation steps may be involved after the reagents are combined, generally ranging from about 1 second to about 72 hours, about 10 seconds to about 24 hours, about 30 seconds to 6 hours, about 2 minutes to 1 hour.

Discussion of Terms

Before proceeding further with the description of examples of specific embodiments of the aforementioned materials and methods, a number of terms employed above will be defined.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc., e.g., phenyl, naphthyl, phenanthryl.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc., e.g., m-methoxyphenyl.

Aralkoxy—an aralkyl radical attached to the remainder of a molecule by an oxygen atom, e.g., benzoxy, 1-naphthylethoxy, etc.

Amine reactive functionality—a functionality reactive with an amine functionality, usually by virtue of nucleophilicity or basicity of the amine, such as, for example, an aldehyde, an α-keto carboxylic acid and the like.

Alkylating agent having a functionality that reacts with an hydroxyl group—a compound that has a functionality reactive with an hydroxyl group, usually by virtue of nucleophilicity of the neutral or ionized hydroxyl group, such as, for example, an oxiranyl radical, an alkyl radical comprising a leaving group such as, for example, halide (bromide, chloride, iodide); aryl sulfonates; alkyl sulfonates; aryl sulfates; alkyl sulfates; tosylates; acrylic acid derivatives such as acrylamide; vinyl sulfones; and the like.

Conjugate—a molecule comprised of two or more substructures bound together, generally through a linking group, to form a single structure.

Analyte—the compound or composition to be detected. The analyte can be comprised of a member of a specific binding pair (sbp) and may be a ligand, which is usually monovalent (monoepitopic), usually haptenic, and is a single compound or plurality of compounds which share at least one common epitopic or determinant site.

The monoepitopic ligand analytes will generally be from about 100 to 2,000 molecular weight, more usually from 125 to 1,000 molecular weight. The analytes include drugs, metabolites, pesticides, pollutants, and the like. Representative analytes, by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid (MPA), and so forth; (ix) vitamins such as A, B, e.g. B12, C, D, E and K, folic acid, thiamine; (x) prostaglandins, which differ by the degree and sites of hydroxylation and unsaturation; (xi) tricyclic antidepressants, which include imipramine, dismethylimipramine, amitriptyline, nortriptyline, protriptyline, trimipramine, chlomipramine, doxepine, and desmethyldoxepin; (xii) anti-neoplastics, which include methotrexate; (xiii) antibiotics, which include penicillin, chloromycetin, actinomycetin, tetracycline, terramycin, the metabolites and derivatives; (xiv) nucleosides and nucleotides, which include ATP, NAD, FMN, adenosine, guanosine, thymidine, and cytidine with their appropriate sugar and phosphate substituents; (xv) miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives; (xvi) metabolites related to diseased states include spermine, galactose, phenylpyruvic acid, and porphyrin Type 1; (xvii) aminoglycosides, such as gentamicin, kanamicin, tobramycin, and amikacin; and (xviii) pesticides such as polyhalogenated biphenyls, phosphate esters, thiophosphates, carbamates, polyhalogenated sulfenamides, their metabolites and derivatives.

Polyvalent analytes are normally poly(amino acids), i.e., polypeptides and proteins, polysaccharides, nucleic acids, and combinations thereof. Such combinations include components of bacteria, viruses, chromosomes, genes, mitochondria, nuclei, cell membranes and the like. For the most part, the polyepitopic ligand analytes will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, a-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For receptor analytes, the molecular weights will generally range from about 10,000 to about $2 \times 10^8$, more usually from about 10,000 to about $10^6$. For immunoglobulins, IgA, IgG, IgE and IgM, the molecular weights will generally vary from about 160,000 to about $10^6$. Enzymes will normally range from about 10,000 to about 1,000,000 in molecular weight. Natural receptors vary widely, generally being at least about 25,000 molecular weight and may be about $10^6$ or higher molecular weight, including such materials as avidin, DNA, RNA, thyroxine binding globulin, thyroxine binding prealbumin, transcortin, etc.

The term analyte further includes oligonucleotide and polynucleotide analytes such as m-RNA, r-RNA, t-RNA, DNA, DNA-RNA duplexes, etc.

The analyte may be a molecule found directly in a sample such as biological tissue, including body fluids, from a host. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium that does not interfere with an assay. An aqueous medium is preferred.

The analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay.

The biological tissue includes excised tissue from an organ or other body part of a host and body fluids, for example, urine, whole blood, plasma, serum, saliva, semen, stool, sputum, cerebral spinal fluid, tears, mucus, and the like. IN many instances, the sample is plasma or serum.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. Polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Hapten—a compound capable of binding specifically to corresponding antibodies, but does not itself act as an immunogen (or antigen) for preparation of the antibodies. Antibodies which recognize a hapten can be prepared against compounds comprised of the hapten linked to an immunogenic (or antigenic) carrier. Haptens are a subset of ligands.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Antibody—an immunoglobulin that specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Substituted—means that a hydrogen atom of a molecule has been replaced by another atom, which may be a single atom such as a halogen, etc., or part of a group of atoms forming a functionality as described above. Such substituent may be a group or functionality imparting hydrophilicity. As discussed above, hydrophilicity may be achieved by a functional group having one or more atoms such as oxygen, nitrogen, sulfur, phosphorus, and so forth; such groups include sulfonate, sulfate, phosphate, amidine, phosphonate, carboxylate, hydroxyl particularly polyols, amine, ether, amide, and the like.

Signal producing system ("sps")—one or more components, at least one component being a detectable label, which generate a detectable signal that relates to the amount of bound and/or unbound label, i.e. the amount of label bound or not bound to the compound being detected. The label is any molecule that produces or can be induced to produce a signal, and may be, for example, a fluorescer, radio-label, enzyme, chemiluminescer or photosensitizer. Thus, the signal is detected and/or measured by detecting enzyme activity, luminescence, light absorbance or radioactivity as the case may be.

Suitable labels include, by way of illustration and not limitation, enzymes such as alkaline phosphatase, glucose-6-phosphate dehydrogenase ("G6PDH") and horseradish peroxidase; ribozyme; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}I$, $^{131}I$, $^{14}C$, $^{3}H$, $^{57}Co$ and $^{75}Se$; particles such as latex or carbon particles; metal sol; crystallite; liposomes; cells, etc., which may be further labeled with a dye, catalyst or other detectable group. Suitable enzymes and coenzymes are disclosed in Litman, et al., U.S. Pat. No. 4,275,149, columns 19–28, and Boguslaski, et al., U.S. Pat. No. 4,318,980, columns 10–14; suitable fluorescers and chemiluminescers are disclosed in Litman, et al., U.S. Pat. No. 4,275,149, at columns 30 and 31; which are incorporated herein by reference.

There are numerous methods by which the label can produce a signal detectable by external means, desirably by visual examination, for example, by electromagnetic radiation, heat, and chemical reagents. The label or other sps members can also be bound to an sbp member, another molecule or to a support.

Labels include groups detectable by means of electromagnetic radiation or by electrochemical detection including dyes, fluorescers, chemiluminescers, and radioactive isotopes.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al., U.S. Pat. No. 5,185,243, columns 11–13, incorporated herein by reference.

The label and/or other sps member may be bound to an sbp member or to a support. For example, the label can be bound covalently to an sbp member such as, for example, an antibody; a receptor for an antibody, a receptor that is capable of binding to a small molecule conjugated to an antibody, or a ligand analog. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal. Methods of conjugation are well known in the art. See, for example, Rubenstein, et al., U.S. Pat. No. 3,817,837, incorporated herein by reference.

Assay—method for the determination of the presence or amount of an analyte.

Measuring the amount of an analyte—quantitative, semi-quantitative, and qualitative methods as well as all other methods for determining an analyte are considered to be methods of measuring the amount of an analyte. For example, a method, which merely detects the presence or absence of an analyte in a sample suspected of containing the analyte, is considered to be included within the scope of the present invention. The terms "detecting" and "determining," as well as other common synonyms for measuring, are contemplated within the scope of the present invention.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

Wholly or partially sequentially—when various agents are combined other than concomitantly (simultaneously), one or more may be combined with one or more of the remaining agents to form a subcombination.

The invention is demonstrated further by the following illustrative examples.

EXAMPLES

Parts and percentages herein are by weight unless otherwise indicated. Temperatures are in degrees Centigrade (° C.).

Abbreviations:
EDTA—ethylenediamine tetraacetic acid
CTNI—Tropinin C
HAMA—human antimouse antibody
BSA—bovine serum albumin
MES—2-morpholinoethanesulfonic acid
PBS—phosphate buffered saline at physiological pH and ionic strength
CMO—carboxymethoxyamine
CV—coefficient of variation
HEPES buffer—
kDa—kilodalton
NSB—non-specific binding Materials:

Chemicals:

Unless noted otherwise, all chemicals were purchased from the Sigma-Aldrich Company (St. Louis Mo.). HAMA blockers were purchased from Roche Diagnostics Corporation (Roche Applied Science, Indianapolis Ind.) and from Scantibodies Laboratory, Inc. 9336 Abraham Way Santee, Calif. 92071 USA. The grade of BSA used for conjugation reactions is known as "fatty acid free" BSA.

Test Samples:

Samples from a local blood bank were screened to determine if they produced a response with the troponin assay. Any donor sample that produced a positive result with the troponin test was assumed to be a false positive. This was confirmed by testing all samples that gave positive responses with at least one commercially available reference method. For the results reported here, the test results were confirmed using the Dade Behring DIMENSION Rxl® troponin (CTNI) test. The false positive samples were further screened for known causes of false positivity. The primary root cause of false positive results is human antibodies that bind mouse antibodies, an interference known as "HAMA" (Human Anti-Mouse Antibodies). The screening process used to determine if samples have HAMA interference consists of adding known HAMA binders (also known as blocking agents) that are available commercially from Roche and Scantibodies. If a sample that gives a positive response becomes normal when HAMA binders are added to the sample, the sample is assumed to be a false positive due to HAMA. Some samples were not corrected by the addition of HAMA binders. These were used in the testing described in the following examples.

Test Assays:

An assay for CTNI, described in "Quantitation of Cardiac Markers by LOCI™ Technology", R. Bauer, et al., (Clinical Chemistry 2004; 50(6 supplement): A5) was used for evaluation of the candidate blocker compounds. The reagents for doing this assay consist of an antibody coated acceptor latex (acceptor bead) that emits light when contacted by singlet oxygen, a biotinylated antibody, and a streptavidin coated donor latex that produces singlet oxygen when illuminated by light of wavelengths that are absorbed by a photosensitizer dye dissolved in the latex particles. The streptavidin of the donor latex was bound to the latex particles through a spacer of dextran with aldehyde linking groups. In the case of the acceptor beads, the antibody was connected to the particles through a linking group or spacer that results from a combination of aminodextran and dextranaldehyde. For both latex reagents, the excess aldehyde groups remaining after linkage of the proteins are reacted with carboxymethoxyamine to quench the aldehydes.

These reagents are packaged in FLEX® containers that serve as reservoirs for the VISTA™ automated clinical analyzer that is described in "Development and Initial Performance of a New High-Volume Multi-Detector Analyzer: The DIMENSION VISTA™ Integrated System", T. Evers, et al. (Clinical Chemistry 2004; 50(6 supplement)) A31. The test kits and the analyzer are available from Dade Behring Inc., Newark, Del., USA. Candidate blocking reagents (soluble protein-polysaccharide conjugates (preformed or formed in situ) that reduce or eliminate interference from sample components) were tested by adding them (or a precursor such as, e.g., dextran aldehyde) to the biotinylated antibody reagent in prototype FLEX® containers or in some cases directly to the sample. FLEX® containers are from Dade Behring Inc.

Each test result shown in the tables below is the average of four test results. In general, the precision of the measurements was <2% CV for calibrators and for measurements of discrepant samples in those cases where effective blockers were used. The testing was done on different days with different instruments, so many control tests were needed to enable comparison of different sets of data.

Example 1

Synthesis of Soluble Protein-Polysaccharide Conjugate

Part A: Synthesis of Dextranaldehyde

One hundred grams (100 g) of 100–200 kDa dextran was added slowly with stirring to 400 mL of deionized water containing 0.5 g of EDTA in a 1 L round bottom flask equipped with a nitrogen purge. To this mixture, 40 g of NaOH was added followed by 15 mL of 2-(4-chlorobutyl)-1.3-dioxolane. The mixture was heated to 90° and held at that temperature with stirring for 24 hours. At this time, 250 mL of water was added, and the mixture was cooled to room temperature using an ice bath. The pH was then adjusted to 6.0–6.5 by slowly adding 12N HCl with stirring. The mixture was then purified by diafiltration using a hollow fiber diafiltration cartridge having a molecular weight cutoff of 10,000 Daltons. A total of 60 L of deionized water was exchanged in the process. The intermediate dioxolane was removed from the diafiltration apparatus, and the volume was adjusted to 1200 mL.

Toluenesulfonic acid (68.5 g) was added to the dioxolane solution, and the pH was adjusted to 1.8 with pyridine. The mixture was allowed to stand for 16 hours at room temperature, and then the pH was adjusted to 6.0 with 1N NaOH. It was purified again using a hollow fiber 10,000 Dalton cutoff diafiltration cartridge, by exchange of 125 L of water.

After removal of the product from the diafiltration system, its concentration was adjusted to approximately 50 mg/mL, and then buffered to pH 7.0 by addition of 0.69 mg/mL of monobasic sodium phosphate monohydrate and 0.71 mg/mL of anhydrous dibasic sodium phosphate. The solids content was determined to be 45.9 mg/mL.

The same procedure was used with 500 kDa dextran to make a higher molecular weight version of dextranaldehyde.

Part B: Synthesis of Dextranaldehyde/Protein Conjugates

The same general synthesis scheme as described in Part A was used for a series of different conjugates that differed in the ratio of dextranaldehyde to protein, the molecular weight of the dextranaldehyde, and the type of protein. The nomenclature used to identify the composition of the candidate soluble conjugates is: xxmwtDexal-proteinyymg/100 mg of dextranaldehyde. For example, 100–200-dexal-BSA-30 would be a product made with dextranaldehyde prepared from 100–200 kDa dextran that had been conjugated with BSA at a ratio of 100 parts dextranaldehyde to 30 parts BSA.

Preparation of 100–200 dexal-BSA30: 1.5 mL of a solution of 20 mg/mL BSA in pH 6.0, 50 mM MES buffer was added with stirring to 2.18 mL of a dextranaldehyde solution containing 100 mg. After the addition was complete, 0.3 mL of a 100 mg/mL solution of sodium cyanoborohydride was added with stirring. The mixture was put in a shaker air bath and held at 37° C. for 18 hours. It was then put in a 6000–8000 molecular weight cutoff dialysis bag and dialyzed against 1 L of deionized water, which was exchanged three times. The final, fourth exchange was against 1 L of pH 6.0 50 mM MES buffer.

Part C: Synthesis of Carboxymethyl Dextranaldehyde Oxime

One (1) mL of a 1M solution of carboxymethoxylamine hemihydrochloride was added to a solution of 100 mg of 100–200 kDa dextranaldehyde in 2.18 mL, and the mixture was incubated at 37° C. for 2 hours. It was then put in a 6000–8000 molecular weight cutoff dialysis bag and dialyzed against 1 L of deionized water, which was exchanged three times. The duration between exchanges was 3–4 hours. The final, fourth exchange was against 1 L of pH 6.0 50 mM MES buffer.

Part D: Synthesis of Dextranaldehyde Modified with Aliphatic Amines

The process for preparing dextranaldehyde modified by different amines was essentially the same, using different amines, at different concentrations. Table 1 below lists the quantities and the amines that were used.

TABLE 1

| Amine | MW | Quantity used | μmoles used |
|---|---|---|---|
| Ethanolamine | 61 | 22.5 mg | 369 |
| Methyl amine | 31 | 33 μL | 369 |

The amine was added with stirring to 100 mg of dextranaldehyde in 2.18 mL, followed by 0.3 mL of a stock solution of 100 mg/mL in water and the mixture was incubated for two hours at 37° C. It was then put in a 6000–8000 molecular weight cutoff dialysis bag and dialyzed against 1 L of deionized water, which was exchanged three times. The duration between exchanges was 3–4 hours. The final, fourth exchange was against 1 L of pH 6.0 50 mM MES buffer.

Example 2

Immunoassay Testing

Part A: Comparative Blocking Activity of Dextran and Dextranaldehyde/BSA Conjugate Formed in Situ in an Assay for Troponin Dextranaldehyde reacts with proteins to form Schiff's bases between the aldehyde functionality and the lysine amino groups of proteins thereby producing a conjugate. This reaction was accomplished by adding 5 mg/mL 500 kDa dextranaldehyde to the biotinylated antibody reagent of the CTNI FLEX® container, which contains 50 mg/mL of BSA in a pH 7.2 HEPES buffer with 1 mg/mL 100–200 KDa dextran. The effect of the addition on the response of the assay to both calibrators (Cal 0 representing 0 ng/ml of troponin and Cal 8.3 representing 8.3 ng/ml troponin) and discrepant false positive samples (identified as NSB 1–29) is seen in Table 2 below.

TABLE 2

| | No Dextranaldehyde | | Dextranaldehyde Added | |
|---|---|---|---|---|
| Samples: | Mean counts | counts ratio, NSB/Cal0 | Mean counts | counts ratio, NSB/Cal0 |
| Cal 0 ng/mL | 7,978 | N/A | 7857 | N/A |
| Cal 8.3 ng/mL | 1,026,400 | N/A | 989444 | N/A |
| NSB 1 | 767,083 | 96.15 | 10507 | 1.34 |
| NSB 3 | 87,991 | 11.03 | 10049 | 1.28 |
| NSB 7 | 44,076 | 5.52 | 9247 | 1.18 |
| NSB 15 | 30,810 | 3.86 | 7920 | 1.01 |
| NSB 16 | 20,211 | 2.53 | 7666 | 0.98 |
| NSB 17 | 93,031 | 11.66 | 7715 | 0.98 |
| NSB 18 | 14,232 | 1.78 | 7533 | 0.96 |
| NSB 20 | 61,782 | 7.74 | 8589 | 1.09 |
| NSB 21 | 319,324 | 40.03 | 8284 | 1.05 |
| NSB 23 | 119,889 | 15.03 | 7771 | 0.99 |
| NSB 26 | 24,607 | 3.08 | 8081 | 1.03 |
| NSB 27 | 24,662 | 3.09 | 7431 | 0.95 |
| NSB 29 | 19,800 | 2.48 | 7566 | 0.96 |

The BSA conjugate formed in situ had the effect of nearly bringing the falsely elevated results to the same level as the zero calibrator ("Cal 0 ng/mL"). Only samples NSB 1, 3, 7, and 20 remained significantly elevated above the background. By comparison, the data show that unmodified dextran was relatively ineffective for blocking the nonspecific binding.

Table 3 below shows the effect of adding 20 mg/mL of two different molecular weight grades of dextran using the same protocol as above:

TABLE 3

| Sample | Mean | counts ratio, NSB/Cal0 |
|---|---|---|
| 20 mg/mL of Dextran 500 | | |
| Cal 0 | 8,237 | N/A |
| Cal 8 | 1,273,769 | N/A |
| NSB 1 | 13,082 | 1.59 |
| NSB 3 | 11,440 | 1.39 |
| NSB 7 | 8,691 | 1.06 |
| 20 mg/mL of Dextran 100–200 | | |
| Cal 0 | 7,392 | N/A |
| Cal 8 | 953,703 | N/A |
| NSB 1 | 18,736 | 2.53 |
| NSB 3 | 9,613 | 1.30 |
| NSB 7 | 8,006 | 1.08 |

In this example, the dextran was added to both the biotinylated antibody reagent and the acceptor bead reagent and Cal 0 represented a calibrator solution having 0 ng/ml of troponin and Cal 8 represented a calibrator solution having 8.3 ng/ml troponin. There was some improvement compared to the case where no additional dextran was added, but the improvement seen was significantly less than with the soluble protein-polysaccharide conjugate, i.e., dextranaldehyde/BSA Schiff's base conjugate, of embodiments of the invention.

Part B: Testing of Dextranaldehyde/Protein Conjugates

As will be seen in examples below, results with the in situ conjugate, which was used as a control for other experiments, were variable from run-to-run. This could be due to the fact that the Schiff's base that forms is unstable and spontaneously dissociates and re-associates. For in situ formation of the soluble conjugate, the dextran aldehyde should either be added to the sample before the first assay reagent or to the reagent that is first mixed with the patient sample. In the case where the in situ conjugate is formed in the reagent, the reagent should contain a protein such as BSA or the like at a concentration of at least 0.5 mg/mL, at least 1 mg/mL, at least 1.5 mg/mL, at least 2.0 mg/mL, and so forth.

In the first experiment, the candidate blocker materials were added to the calibrators and the NSB-1 discrepant sample, and the mixture was held for a half an hour before testing was done. The candidate blockers were added to give a concentration of 1 mg/mL by adding 5 μL of a 20 mg/mL stock to 0.1 mL of sample. The reagent for the control condition identified as "PBS control" was prepared by diluting the biotinylated antibody reagent to the same extent as the tests with phosphate buffered saline (10 mM sodium phosphate, 120 mM sodium chloride, 7.2 mM potassium chloride, pH 7.2). The results are shown below in Table 4.

TABLE 4

| Additive | Test Result Counts | | | % supression* |
|---|---|---|---|---|
| | Cal 0 | Cal 8 | NSB 1 | |
| PBS as control | 8,916 | 979,811 | 999,031 | 0.0% |
| 500-Dextran aldehyde | 8,809 | 864,795 | 9,950 | 99.88% |
| 100–200-Dexal-BSA-10 | 8,389 | 954,766 | 26,160 | 98.2% |
| 100–200-Dexal-BSA-30 | 8,460 | 969,563 | 11,242 | 99.7% |

*% supression = 1 − (test NSB 1 − test cal 0)/(control NSB 1 − Cal 0)

While most of the non-specific elevation was eliminated with the three blockers above, there was still a small false positive signal with the NSB-1 sample. The above results may be acceptable for many assays; however, a troponin assay has higher demands for interference control than many other assays.

Additional conjugates were made using a higher level of BSA in the synthesis, different proteins and also higher molecular weight dextranaldehyde. The additives were put into the biotinylated antibody reagent at a concentration of 5 mg/mL. The results of testing of these conjugates are summarized in Table 5 below:

TABLE 5

| | Test Result Counts | | | % supression* |
|---|---|---|---|---|
| | Cal 0 | Cal 8 | NSB 1 | |
| Run 1 Additive | | | | |
| PBS (control) | 7,232 | 733,189 | 889,128 | 0.0% |
| 100–200-Dexal-BSA-50, first lot | 6,578 | 743,213 | 7,005 | 99.95% |
| 100–200-Dexal-BSA-50, second lot | 7,136 | 807,327 | 7,134 | 100.00% |

TABLE 5-continued

| | Test Result Counts | | | % supression* |
|---|---|---|---|---|
| | Cal 0 | Cal 8 | NSB 1 | |
| 100–200-Dexal-BSA-100 | 7,320 | 823,386 | 7,544 | 99.97% |
| 100–200-Dexal-Murine IgG-20 | 6,619 | 794,745 | 7,909 | 99.85% |
| Run 2 Additive | | | | |
| PBS (control) | 7,177 | 707,027 | 823,326 | 0.00% |
| 100–200-Dexal-ovalbumin-100 | 6,370 | 734,218 | 39,569 | 95.93% |
| 100–200-Dexal-ovalbumin-50 | 6,573 | 749,661 | 12,630 | 99.26% |

*% supression = 1 − (test NSB 1 − test cal 0)/(control NSB 1 − Cal 0)

While these data show in this experiment that the most effective blocker of the series of protein conjugates was the one based upon BSA, other proteins also resulted in conjugates that exhibited effective blocking of interference. In addition, in this experiment, performance of the conjugates appears to reach a plateau when the ratio of dextranaldehyde to BSA in the synthesis is in the range of 2:1 to 1:1. It should be noted that the above ratio range is for dextranaldehyde and BSA. In general, the ratio will depend on the nature of the polysaccharide such as, e.g., the chemical composition, molecular weight, etc., and on the nature of the protein such as, e.g., chemical composition, molecular weight, etc.

Part C: Blocking with Small Molecule/Dextran Derivatives:

A series of derivatives were tested to compare the blocking activity of dextran and functionalized dextran to the soluble dextran-protein conjugates of embodiments of the present invention.

Testing of low molecular weight amine derivatives of dextranaldehyde was done by adding these to the samples at a concentration of 1 mg/mL. In the case of the dextranaldehyde additive, the mixture was allowed to stand for half an hour before testing to give time for it to react with the serum proteins of the samples. The comparative assay results are shown in Table 6 below:

TABLE 6

| Additive | Test Result Counts | | | % supression* |
|---|---|---|---|---|
| | Cal 0 | Cal 8 | NSB 1 | |
| PBS as control | 8,916 | 979,811 | 999,031 | 0.0% |
| 500-Dextran aldehyde | 8,809 | 864,795 | 9,950 | 99.88% |
| 100–200-Dexal-ethanolamine | 9,018 | 971,960 | 216,201 | 79.1% |
| 100–200-Dexal-methylamine | 8,690 | 950,346 | 206,471 | 80.0% |

*% supression = 1 − (test NSB 1 − test cal 0)/(control NSB 1 − Cal 0)

The blocking ability of the dextranaldehyde-alkyl amine derivatives was significantly less than the blocking ability of the reaction product of dextranaldehyde with serum proteins of the sample.

The following experiment compared the blocking ability of the reaction product of dextranaldehyde with BSA proteins in the sample to the blocking ability of the carboxymethyloxime (CMO) derivative of dexal, which cannot react with serum proteins. In this case, the test additives were added to the biotinylated antibody reagent at a concentration of 5 mg/mL. The test results are shown in Table 7 below:

TABLE 7

| Additive | Test Result Counts | | | % supression* |
|---|---|---|---|---|
| | Cal 0 | Cal 8 | NSB 1 | |
| PBS (control) | 8,298 | 1,011,502 | 1,049,243 | 0.0% |
| 500 Kdal Dextranaldehyde | 7,857 | 989,444 | 10,507 | 99.7% |
| 100–200-Dexal-CMO | 8,384 | 1,052,110 | 1,026,872 | 2.2% |

*% supression = 1 − (test NSB 1 − test cal 0)/(control NSB 1 − Cal 0)

The Schiffs base reaction product of dextranaldehyde and BSA is significantly more effective at blocking the interference than is the carboxymethyloxime derivative of dexal.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for determining the presence and/or amount of an analyte in a sample suspected of containing said analyte, said method comprising:
   (a) providing in combination said sample, a soluble compound comprising a protein linked to a first polysaccharide, and reagents for detecting said analyte wherein at least one of said reagents comprises a solid support comprising a second polysaccharide wherein said reagents comprise a specific binding partner for said analyte and wherein said protein does not bind to any of said reagents or to said analvte and wherein said first polysaccharide and said second polysaccharide may be the same or different,
   (b) incubating said combination under conditions for binding of said analyte to one or more of said reagents, and
   (c) detecting the presence and/or amount of binding of said analyte to said specific binding partner for said analyte, the presence and/or amount of said binding being related to the presence and/or amount of said analyte in said sample.

2. The method according to claim 1 wherein said soluble compound has a neutral charge or a negative charge.

3. The method according to claim 1 wherein said solid support comprises said specific binding partner for said analyte.

4. The method according to claim 3 wherein said at least one other of said reagents comprises a solid support comprising a second specific binding partner for said analyte.

5. The method according to claim 1 wherein said first polysaccharide and said second polysaccharide are the same.

6. The method according to claim 1 wherein said sample and said soluble compound are mixed together prior to forming said combination.

7. The method according to claim 1 wherein said soluble compound and said solid support are mixed together prior to forming said combination.

8. The method according to claim 1 wherein said first polysaccharide or said second polysaccharide is dextran or a dextran derivative.

9. The method according to claim 1 wherein said protein is a serum protein.

10. The method according to claim 9 wherein said serum protein is an albumin or a gamma globulin.

11. The method according to claim 1 wherein said solid support comprises particles.

12. The method according to claim 1 wherein said second polysaccharide is linked to said solid support and a member of a specific binding pair is linked to said second polysaccharide.

13. A method for determining the presence and/or amount of an analyte in a sample suspected of containing said analyte, said method comprising:
   (a) providing in combination said sample, a soluble compound comprising a protein linked to a dextran or a dextran derivative, and reagents for detecting said analyte wherein at least one of said reagents comprises a solid support comprising a polysaccharide and a specific binding partner for said analyte, wherein said protein does not bind to any of said reagents or to said analyte,
   (b) incubating said combination under conditions for binding of said analyte to said specific binding partner for said analyte, and
   (c) detecting the presence and/or amount of binding of said analyte to said specific binding partner for said analyte, the presence and/or amount of said binding being related to the presence and/or amount of said analyte in said sample.

14. The method according to claim 13 wherein said polysaccharide is a dextran or a dextran derivative.

15. The method according to claim 13 wherein said reagents comprise a second specific binding partner for said analyte.

16. The method according to claim 13 wherein said protein is selected from the group consisting of gamma globulins, albumins, casein and gelatins.

17. The method according to claim 13 wherein said sample and said soluble compound are mixed together prior to forming said combination.

18. The method according to claim 13 wherein said soluble compound and said solid support are mixed together prior to forming said combination.

19. The method according to claim 13 wherein said protein is a an albumin.

20. The method according to claim 13 wherein said solid support comprises particles.

21. The method according to claim 13 wherein said polysaccharide is linked to said solid support and said specific binding partner for said analyte is linked to said polysaccharide.

* * * * *